United States Patent [19]

Tomohiro et al.

[11] Patent Number: 4,673,645
[45] Date of Patent: Jun. 16, 1987

[54] PROCESS AND MICROORGANISMS FOR PRODUCING MITOMYCIN A BY FERMENTATION

[75] Inventors: Susumu Tomohiro, Shizuoka; Yuko Arai, Susono; Kazuyuki Mineura, Matsudo, all of Japan

[73] Assignee: Kyowa Hakko Kogyo Co., Ltd., Tokyo, Japan

[21] Appl. No.: 414,940

[22] Filed: Sep. 3, 1982

[30] Foreign Application Priority Data

Sep. 4, 1981 [JP] Japan .................... 56-138364

[51] Int. Cl.$^4$ ............ C12P 17/18; C12R 1/465; C12N 1/20
[52] U.S. Cl. ......................... 435/119; 435/886; 435/253
[58] Field of Search ............. 435/119, 886, 172.1, 435/253; 548/422

[56] References Cited

U.S. PATENT DOCUMENTS 3,660,578  5/1972  Hata et al. ................ 435/886 X
4,264,504  4/1981  Urakawa et al. ................ 548/422

FOREIGN PATENT DOCUMENTS 0008021  2/1980  European Pat. Off. .
0045322  3/1980  Japan ....................... 435/119

OTHER PUBLICATIONS

Chemical Abstracts, vol. 88, No. 1, 1978, p. 418, Abstract No. 4686t, Abou-Zeid et al.
Umezawa, Index of Antibiotics from Actinomycetes, Tokyo, University of Tokyo Press, 1967, p. 421.
Antibiotics vol. IV: Biosynthesis, Corcoran (ed.), New York, Springer-Verlag, 1981, pp. 295-312.
Wang et al., Fermentation and Enzyme Technology, Wiley & Sons, New York, (1979), pp. 34, 52-53.
Stanier et al., The Microbial World, Prentice Hall, Englewood Cliffs, New Jersey, 1976, pp. 433-434.

Primary Examiner—Sam Rosen
Assistant Examiner—Randall E. Deck
Attorney, Agent, or Firm—Antonelli, Terry & Wands

[57] ABSTRACT

A process for producing mitomycin A by fermentation, which involves culturing a microorganism belonging to the genus Streptomyces, which is capable of producing mitomycin A and having at least one property of (1) deficiency in an ability to produce mitomycin C and (2) a resistance to tryptophan analog, in a culture medium forming and accummulating mitomycin A in the culture medium; and recovering mitomycin A therefrom. The microorganism preferably involves Streptomyces caespitosus T-17-135 (NRRL 12508) or Streptomyces caespitosus (NRRL 12513).

3 Claims, No Drawings

PROCESS AND MICROORGANISMS FOR PRODUCING MITOMYCIN A BY FERMENTATION

This invention relates to a novel process for producing mitomycin A by fermentation, and more particularly to a process for producing mitomycin A by fermentation, which uses a microorganism belonging to the genus Streptomyces, capable of producing mitomycin A and having at least one property of (i) deficiency in an ability to produce mitomycin C and (ii) a resistance to tryptophan analog and to the novel microorganisms belonging to the genus Streptomyces which are capable of producing mitomycin in increased yields. Mitomycin A and derivatives thereof are known as antitumor substances which have a great demand as medicaments.

Heretofore, processes for producing mitomycin A by fermentation have been known (Japanese Published Examined Patent Application Nos. 7597/59 and 19746/61). However, according to these processes, other mitomycins such as mitomycins B, C and F are produced as by-products in a larger amount than mitomycin A, and thus the yield of mitomycin A is low. Accordingly, a process for producing mitomycin A in a higher yield has been desired.

The present inventors have studied a commercial process for producing mitomycin A, have found that, when a certain mutant of the genus Streptomyces is used, mitomycin A is accumulated in a remarkably larger amount without forming mitomycin C in a culture liquor, and have completed the present invention.

The present invention will be described in detail below.

According to the present invention, mitomycin A can be produced in a high yield by culturing a strain belonging to the genus Streptomyces, capable of producing mitomycin A and having at least one property (or characteristic) of a deficiency in an ability to produce mitomycin C and a resistance to tryptophan analog in a culture medium, accumulating a considerable amount of mitomycin A in the culture liquor, and recovering mitomycin A therefrom. The expression "deficiency in an ability to produce mitomycin C" is defined as the case when mitomycin C is not produced at all and the case when mitomycin C is not substantially produced, in microorganism cells as well as in a culture medium.

Any strain can be used, so far as it belongs to the genus Streptomyces and is capable of producing mitomycin A and has at least one property of deficiency in an ability to produce mitomycin C and a resistance to tryptophan analog.

Examples of particularly suitable strains are Streptomyces caespitosus AN-9 and Streptomyces caestopitosus T-17-135. AN-9 and T-17-135 strains were deposited on Aug. 10, 1981 and July 7, 1981, respectively, with the Agricultural Research Culture Collection (NRRL) International Depository Authority under the Budapest Treaty on the International Recognition of the Deposit of Microorganisms and accorded the accession numbers NRRL 12513 and NRRL 12508, respectively, and are available therefrom. These strains are mutants obtained by mutation of Streptomyces caespitosus ATCC 27422 and are representative of the substantially pure or biologically pure cultures that may be utilized for the production of mitomycin A. A specific mutation procedure will be described as follows:

Spores of Streptomyces caespitosus ATCC 27422 which has been cultured on a complete medium (containing 1 g/dl glucose, 0.2 g/dl peptone, 0.1 g/dl meat extract, 0.1 g/dl yeast extract and 2 g/dl agar at pH 7.2) at 28° C. for 5 days, are suspended in a tris-maleate buffer (pH 6.0) containing 200 $\gamma$/ml N-methyl-N'-nitro-N-nitrosoguanidine (hereinafter referred to as "NTG") and the suspension is allowed to stand at room temperature for 1 to 3 hours. The spores are separated, washed, smeared on a complete agar medium and cultured at 28° C. for 3 days. Growing colonies are cultured in a liquid complete medium at 28° C. for 3 days, and the mitomycins thus produced are isolated by thin layer chromatography and subjected to fractionating quantitative determination by a chromato-scanner analyzer whereby only the strains deficient in production of mitomycin C are selected out.

One of the strains is said Streptomyces caespitosus AN-9 (NRRL 12513).

The strain is further subjected to NTG treatment in the same manner as above. The resulting spores are smeared on a complete medium containing 100 $\gamma$/ml tryptophan analog and cultured at 28° C. for 5 days. Growing colonies are separated as mutants having a resistance to tryptophan analog. One of the resulting mutants having a resistance to tryptophan analog is Streptomyces caespitosus T-17-135 (NRRL 12508).

Any synthetic medium or natural medium may be used for culturing the microorganism in the present invention, so far as the medium appropriately contains carbon sources, nitrogen sources, inorganic materials and other nutrients. That is, glucose, fructose, sucrose, blackstrap molasses, starch, glycerine, soybean oil, etc. can be used as a carbon source. Soybean meal, yeast, corn steep liquor, peptone, meat extract, soybean cake, etc. can be used as a nitrogen source.

Culturing is carried out under aerobic conditions, for example, with shaking, with aeration and stirring, etc. Preferable pH is 5 to 8 during the culturing, and sodium hydroxide, calcium carbonate, etc. are used as a pH controlling agent. Culturing is carried out usually at 25° to 35° C. for 3 to 4 days. Isolation of mitomycin A from a culture liquor can be carried out according to the conventional methods, for example, adsorption on an adsorbing agent, solvent extraction, etc.

Practice of specific embodiments of the present invention is illustrated by the following representative examples.

EXAMPLE 1

In this example, 300 ml of a seed culture medium containing 1.5 g/dl glucose, 1 g/dl yeast, 0.5 g/dl starch, 0.5 g/dl sodium chloride and 0.3 g/dl calcium carbonate at pH 7.2 is put into a 2 l-Erlenmeyer flask and sterilized. Then, Streptomyces caespitosus T-17-135 is inoculated in the culture medium and cultured at 28° C. for 3 days with shaking.

On the other hand, 3 l of a fermentation culture medium containing 2 g/dl sucrose, 1 g/dl starch, 4 g/dl soybean meal, 0.5 g/dl sodium chloride and 0.3 g/dl calcium carbonate at pH 7.2 is put into a 5 l-jar fermenter and sterilized. Then, 300 ml of the said seed culture liquor is added to the fermentation culture medium, and cultured at an aeration rate of 3 l/min., a stirring speed of 400 r.p.m. and 30° C. for 3 days.

At the same time, parent strain Streptomyces caespitosus ATCC 27422 is cultured separately under the same conditions as above.

The resulting yields of mitomycins are give in Table 1. The mutant having a resistance to tryptophan analog and a deficiency in an ability to produce mitomycin C has a mitomycin A yield which is about 6 times as high as that of the parent strain, and has no mitomycin C yield at all. Yield proportion of mitomycin A among the mitomycins by the mutant is increased by about 5 times depending upon that by the parent strain, and it is seen that the commercial production of mitomycin A has been made possible.

TABLE 1

| Mitomycins produced | Mutant T-17-135 | Parent strain ATCC 27422 |
| --- | --- | --- |
| Mitomycin A ($\gamma$/ml) | 62 | 11 |
| Mitomycin B ($\gamma$/ml) | 21 | 25 |
| Mitomycin C ($\gamma$/ml) | 0 | 42 |
| Yield proportion of mitomycin A (A/total %) | 75 | 14 |

The mitomycins A, B and C are detected by concentrating the cell-free culture liquor to 50-fold, subjecting the concentrated culture liquor to silica gel thin layer chromatography (silica gel: Merck 5721, 10 $\mu$l spot, developer: ethyl acetate-acetone (3:2 by volume)) and subjecting the resultant chromatograph to fractionating quantitative determination by a chromato-scanner. The detectable limit concentration is 1 $\gamma$/ml in the foregoing detecting procedure.

EXAMPLE 2

In this example, 3 l of the fermentation liquor wherein *Streptomyces caespitosus* T-17-135 is cultured, as obtained in Example 1 is immediately centrifuged to remove cells.

Then, 20 g of active carbon is added to the filtrate to adsorb mitomycins. The active carbon is separated and 80 ml of acetone is added thereto. The mixture is stirred approximately at pH 6 for extraction, and the extract is concentrated at 50° C. or below. The concentrate is passed through an alumina column, and adsorbed mitomycins are chromatographically eluted with chloroform solutions of methanol whose concentration is varied.

Mitomycin A fractions are then passed through an alumina column, and mitomycin A is extracted with ethyl acetate. The extract is concentrated under reduced pressure at 50° C. or below whereby 36 mg of crystals of mitomycin A is obtained.

EXAMPLE 3

In this example, 500 ml of a seed medium containing 1 g/dl glucose, 1 g/dl yeast, 0.5 g/dl starch, 0.5 g/dl sodium chloride and 0.3 g/dl calcium carbonate at pH 7.2 is poured into a 2 l-Erlenmeyer flask and sterilized. Then, *Streptomyces caespitosus* AN-9 (NRRL 12513) is inoculated on the seed medium, and cultured at 28° C. for 3 days with shaking.

On the other hand, 30 l of a fermentation medium containing 2 g/dl fructose, 1 g/dl starch, 4 g/dl soybean meal, 0.5 g/dl sodium chloride and 0.5 g/dl calcium carbonate at pH 7.2 is poured in a 50 l-jar fermenter, and sterilized. Then, 300 ml of the seed culture liquor is added to the fermentation medium, and cultured with aeration stirring at an aeration rate of 15 l/min., a stirring speed of 300 r.p.m., and 30° C. for 3 days.

At the same time, parent strain *Streptomyces caespitosus* ATCC 27422 is cultured separately under the same conditions as above.

Yield of mitomycin A is 10 $\gamma$/ml with the parent strain ATCC 27422; whereas it was 18 $\gamma$/ml with the mutant AN-9, which is approximately double of the former.

The parent strain ATCC 27422 by-produces 19 $\gamma$/ml mitomycin C; whereas the mutant AN-9 by-produces no mitomycin C.

What is claimed is:

1. A biologically pure culture of *Streptomyces caespitosus* AN-9 (NRRL 12513).

2. A biologically pure culture of *Streptomyces caespitosus* T-17-135 (NRRL 12508).

3. A process for producing mitomycin A by fermentation, which comprises culturing *Streptomyces caespitosus* T-17-135 (NRRL 12508) or *Streptomyces caespitosus* AN-9 (NRRL 12513) in a culture medium, allowing the accumulation of mitomycin A in the culture medium, and recovering mitomycin A therefrom.

* * * * *